(12) United States Patent
Horii et al.

(10) Patent No.: US 7,226,790 B2
(45) Date of Patent: Jun. 5, 2007

(54) METHOD FOR MEASUREMENT USING SODIUM AZIDE

(75) Inventors: Miki Horii, Kyoto (JP); Kaori Ishimaru, Kyoto (JP)

(73) Assignee: Arkray, Inc., Kyoto (JP)

( * ) Notice: Subject to any disclaimer, the term of this patent is extended or adjusted under 35 U.S.C. 154(b) by 104 days.

(21) Appl. No.: 10/490,900

(22) PCT Filed: Oct. 9, 2002

(86) PCT No.: PCT/JP02/10464

§ 371 (c)(1),
(2), (4) Date: Mar. 26, 2004

(87) PCT Pub. No.: WO03/033730

PCT Pub. Date: Apr. 24, 2003

(65) Prior Publication Data

US 2004/0209378 A1 Oct. 21, 2004

(30) Foreign Application Priority Data

Oct. 11, 2001 (JP) ............................. 2001-314217

(51) Int. Cl.
*G01N 33/72* (2006.01)
(52) U.S. Cl. .................... 436/67; 436/66; 436/164; 436/166; 436/86; 435/25
(58) Field of Classification Search ................ 436/63, 436/66, 67, 164, 166, 163, 86; 435/25
See application file for complete search history.

(56) References Cited

U.S. PATENT DOCUMENTS 4,748,115 A 5/1988 Steaffens
6,352,835 B1 * 3/2002 Komori et al. ............... 435/25
6,790,665 B2 * 9/2004 Yonehara et al. ............ 436/66
2004/0157285 A1 * 8/2004 Ishimaru et al. ........... 435/40.5

FOREIGN PATENT DOCUMENTS

| EP | 0 166 505 | 4/1985 |
| EP | 0 919 632 A2 | 6/1999 |
| EP | 1 464 643 A1 | 10/2004 |
| JP | 60-214900 | 10/1985 |
| JP | 6-253899 | 9/1994 |

OTHER PUBLICATIONS

Johnson et al., "Fructosamine: a new approach to the estimation of serum glycosylprotein. An index of diabetic control." *Clinica Chimica Acta.*, 1982, vol. 127, pp. 87-95.
Greger, et al., "Measurement of Oxidative Activity in Hemocytes of the Pacific Razor Clam, *Siliqua patula*, and the Oyster, *Crassostrea gigas*, Using Lucigenin- and Luminol-Dependent Chemiluminescence", J. of Invertebrate Pathology 65, 48-60 (1995).

* cited by examiner

*Primary Examiner*—Maureen M. Wallenhorst
(74) *Attorney, Agent, or Firm*—Hamre, Schumann, Mueller & Larson, P.C.

(57) ABSTRACT

A method of measuring an analyte in a sample with excellent sensitivity using a redox reaction is provided. In this method, a reducing substance or an oxidizing substance derived from the analyte is measured in the presence of a tetrazolium compound and sodium azide using the redox reaction, and an amount of the analyte is determined from the amount of the reducing substance or oxidizing substance thus measured. The tetrazolium compound and the sodium azide are present at a ratio in a range from 20:3 to 20:12. Preferably, a solution containing the tetrazolium compound and the sodium azide is aged and then added to the sample.

11 Claims, 3 Drawing Sheets

METHOD FOR MEASUREMENT USING SODIUM AZIDE

TECHNICAL FIELD

The present invention relates to a method for measurement using a redox reaction.

BACKGROUND ART

Conventionally, measurement of the amount of an analyte in a sample using a redox reaction has been utilized for a wide range of applications. For example, such measurement has been utilized for measuring glycated proteins in applications such as biochemical analyses, clinical tests, and the like.

For example, glycated proteins in blood, especially glycated hemoglobins in erythrocytes, serve as important indexes in the diagnosis, treatment, etc. of diabetes, because they reflect the patient's past history of blood glucose levels. Such glycated proteins in erythrocytes are measured utilizing a redox reaction, for example, in the following manner.

First, erythrocytes are hemolyzed to prepare a sample. Then, this hemolyzed sample is treated with a fructosyl amino acid oxidase (hereinafter referred to as "FAOD") so that the FAOD acts on a glycation site of a glycated protein to form hydrogen peroxide. The amount of the hydrogen peroxide corresponds to the amount of the glycated protein. Subsequently, a peroxidase (hereinafter referred to as "POD") and a reducing agent are added to the sample, so that a redox reaction occurs between the hydrogen peroxide and the reducing agent with the POD as a catalyst. At this time, when a reducing agent that develops color when it is oxidized is used, the amount of the hydrogen peroxide can be determined by measuring the color developed. As a result, the amount of the glycated protein in the erythrocytes can be determined.

DISCLOSURE OF INVENTION

However, depending on the sample used, the conventional methods may not exhibit sufficient measurement sensitivity and thus may fail to improve the accuracy of the measurement. Furthermore, since glycated proteins in blood serve as important indexes in the diagnosis, treatment, etc. of diabetes as described above, still further improvement in the accuracy of measurement is desired in methods of measuring them using a redox reaction.

Therefore, it is an object of the present invention to provide a method of measuring an analyte in a sample with high sensitivity using a redox reaction.

In order to achieve the above object, the present invention provides a method of measuring an analyte in a sample using a redox reaction, including: measuring an amount of a reducing substance or an oxidizing substance derived from the analyte in the presence of a tetrazolium compound and sodium azide using the redox reaction; and determining an amount of the analyte from the amount of the reducing substance or oxidizing substance thus measured. By carrying out the measurement in the presence of the tetrazolium compound and the sodium azide as described above, the measurement sensitivity can be improved, although the mechanism is unknown. In the present invention, "a reducing substance or an oxidizing substance derived from an analyte" includes the analyte itself, a reducing/oxidizing substance contained therein, and a reducing/oxidizing substance formed from the analyte using an oxidoreductase or the like.

In the method of the present invention, it is preferable that the tetrazolium compound (A) and the sodium azide (B) are present at a ratio (molar ratio A:B) in a range from 20:3 to 20:12.

In the method of the present invention, it is preferable that a final concentration of the tetrazolium compound in a reaction solution of the redox reaction is in a range from 0.5 to 2.5 mmol/l, and a final concentration of the sodium azide in the reaction solution is in a range from 0.13 to 1.3 mmol/l.

In the method of the present invention, it is preferable that a solution containing the tetrazolium compound and the sodium azide is aged and is then added to the sample because this allows still further improvement in the sensitivity.

It is preferable that the solution is aged at a temperature in a range from 20° C. to 60° C. Furthermore, it is preferable that the solution is aged for at least 6 hours, more preferably for 6 to 120 hours.

In the method of the present invention, it is preferable that the tetrazolium compound is 2-(4-iodophenyl)-3-(2,4-dinitrophenyl)-5-(2,4-disulfophenyl)-2H-tetrazolium salt.

In the method of the present invention, it is preferable that the oxidizing substance derived from the analyte is hydrogen peroxide, and that the amount of the hydrogen peroxide is measured by the redox reaction. The amount of the hydrogen peroxide preferably is measured using an oxidase and a substrate that develops color by oxidation (hereinafter, referred to as a color-developing substrate), for example.

In the method of the present invention, the type of the sample is not particularly limited. The method also can be applied to samples other than whole blood, plasma, serum, and blood cells, e.g., biological samples such as urine and spinal fluid, drinks such as juices, foods such as soy sauce and Worcestershire sauce.

Furthermore, the analyte is not particularly limited as long as a redox reaction is utilized. For example, the analyte may be components in whole blood, components in erythrocytes, components in plasma, components in serum, components in urine, components in spinal fluid, and the like, and it is preferably a component in erythrocytes. For example, when a component in erythrocytes is to be measured, whole blood itself may be hemolyzed to prepare a sample, or erythrocytes may be separated from whole blood and hemolyzed to prepare a sample. Examples of the analyte include glycated proteins such as glycated hemoglobins and glycated albumins, glycated peptides, glycated amino acids, glucose, uric acid, cholesterol, creatinine, sarcosine, and glycerol. Among these, glycated proteins are more preferable.

In the method of the present invention, when the analyte is a glycated protein, it is preferable that a glycation site thereof is degraded by oxidation with FAOD so that hydrogen peroxide is formed. Also, when the analyte is a glycated peptide or a glycated amino acid, it is preferable that the glycated peptide or the glycated amino acid similarly is subjected to the action of FAOD. Moreover, it is preferable that glycated proteins and glycated peptides are treated with a protease prior to the FAOD treatment as necessary.

BEST MODE FOR CARRYING OUT THE INVENTION

Figure 1:
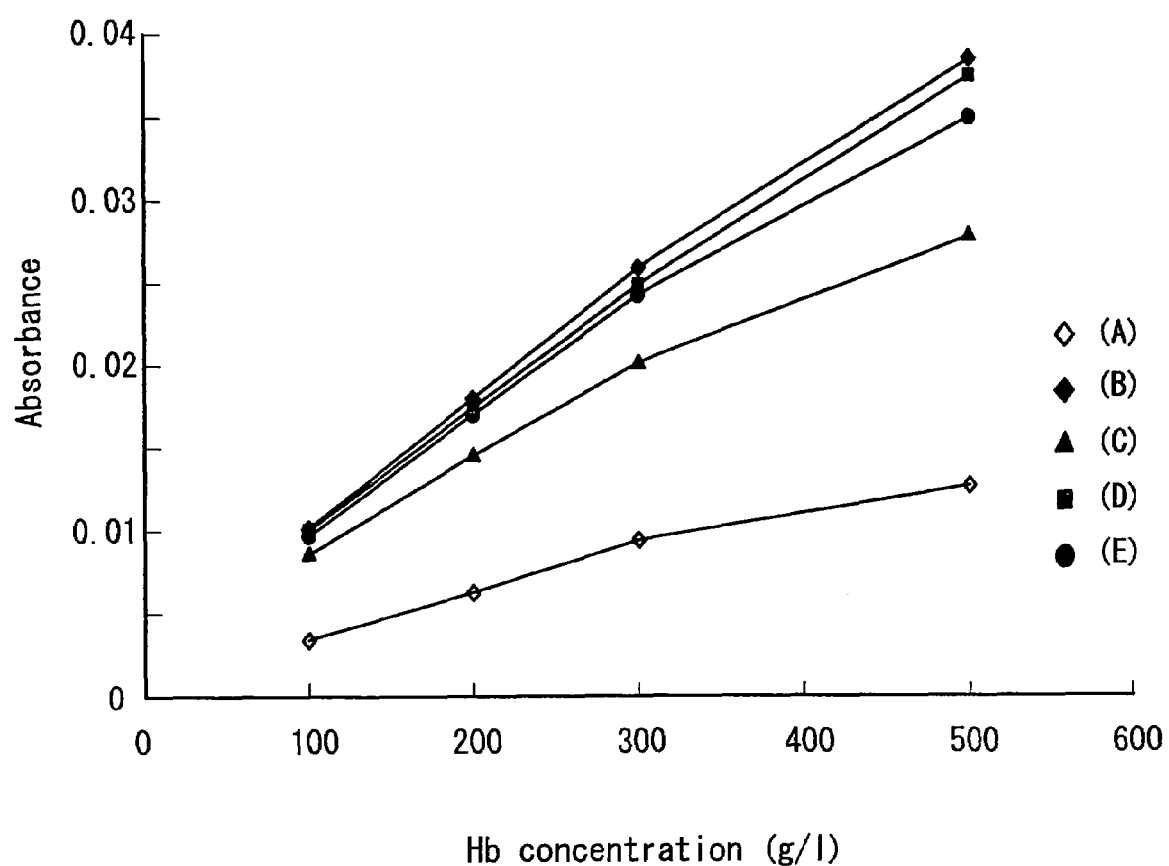
FIG. 1 is a graph showing the correlation between a molar ratio at which a tetrazolium compound and sodium azide are added, a Hb concentration, and an absorbance in one example of a method for measurement according the present invention.

The tetrazolium compound used in the present invention preferably contains ring substituents at least at two positions on its tetrazole ring, more preferably at three positions on its tetrazole ring, for example.

In the case where the tetrazolium compound contains ring substituents at least at two positions on its tetrazole ring as described above, it is preferable that the ring substituents are at the 2-position and 3-position on the tetrazole ring. Further, in the case where the tetrazolium compound contains ring substituents at three positions on its tetrazole ring, it is preferable that the ring substituents are at the 2-position, 3-position, and 5-position on the tetrazole ring.

Further, it is preferable that at least two ring substituents of the tetrazolium compound have a benzene ring structure. Other than the benzene ring structure, the ring substituents may have a resonance structure with S or O being contained in the ring skeleton, for example. Examples of the ring substituents with such a resonance structure include a thienyl group, thiazoyl group, and the like.

Furthermore, it is preferable that the tetrazolium compound contains ring substituents at least at three positions on its tetrazole ring and at least two of the ring substituents have a benzene ring structure.

Still further, it is preferable that at least one ring substituent contains a functional group, and a larger number of functional groups are more preferable.

As the functional group, an electron-withdrawing functional group preferably is used. For example, a halogen group, ether group, ester group, carboxy group, acyl group, nitroso group, nitro group, hydroxy group, sulfo group, and the like can be used. Other than these, characteristic groups containing oxygen such as a hydroperoxy group, oxy group, epoxy group, epidioxy group, oxo group, and the like; and characteristic groups containing sulfur such as a mercapto group, alkylthio group, methylthiomethyl group, thioxo group, sulfino group, benzenesulfonyl group, phenylsulfonyl group, p-toluenesulfonyl group, p-tolylsulfonyl group, tosyl group, sulfamoyl group, isothiocyanate group, and the like also can be used, for example. Among these electron-withdrawing functional groups, a nitro group, sulfo group, halogen group, carboxy group, hydroxy group, methoxy group, ethoxy group are preferable. Further, in addition to the above-described electron-withdrawing functional groups, unsaturated hydrocarbon groups such as a phenyl group ($C_6H_5$—), styryl group ($C_6H_5CH{=}CH$—), and the like also can be used, for example. It is to be noted that the functional groups may have been ionized by dissociation.

Still further, it is preferable that the tetrazolium compound contains benzene rings at the 2-position and 3-position on its tetrazole ring and at least one of the benzene rings contains at least one functional group selected from the group consisting of a halogen group, carboxy group, nitro group, hydroxy group, sulfo group, methoxy group, and ethoxy group. It is to be noted here that both the benzene rings may have such a functional group. Further, the functional group may be contained at any positions (ortho-, meta-, pra-) on each of the benzene rings. Furthermore, the number of the functional groups is not particularly limited, and the benzene ring may have either the same or different functional groups.

Examples of the tetrazolium compound containing ring substituents having a benzene ring structure at the 2-position, 3-position, and 5-position on its tetrazole ring include:

2-(4-iodophenyl)-3-(4-nitrophenyl)-5-(2,4-disulfophenyl)-2H-tetrazolium salt;

2-(4-iodophenyl)-3-(2,4-dinitrophenyl)-5-(2,4-disulfophenyl)-2H-tetrazolium salt;

2-(2-methoxy-4-nitrophenyl)-3-(4-nitrophenyl)-5-(2,4-disulfophenyl)-2H-tetrazolium salt;

2-(4-iodophenyl)-3-(4-nitrophenyl)-5-phenyl-2H-tetrazolium salt;

3,3'-(1,1'-biphenyl-4,4'-diyl)-bis(2,5-diphenyl)-2H-tetrazolium salt;

3,3'-[3,3'-dimethoxy-(1,1'-biphenyl)-4,4'-diyl]-bis[2-(4-nitrophenyl)-5-phenyl-2H-tetrazolium salt];

2,3-diphenyl-5-(4-chlorophenyl) tetrazolium salt;

2,5-diphenyl-3-(p-diphenyl) tetrazolium salt;

2,3-diphenyl-5-(p-diphenyl) tetrazolium salt;

2,5-diphenyl-3-(4-styrylphenyl) tetrazolium salt;

2,5-diphenyl-3-(m-tolyl) tetrazolium salt; and 2,5-diphenyl-3-(p-tolyl) tetrazolium salt.

The tetrazolium compound is not limited to those described above. In addition to the above-described tetrazolium compounds, a tetrazolium compound containing ring substituents having a benzene ring structure at two positions and a ring substituent having a structure other than the benzene ring structure at one position on its tetrazole ring also may be used. Examples of such a tetrazolium compound include:

2,3-diphenyl-5-(2-thienyl) tetrazolium salt;

2-benzothiazoyl-3-(4-carboxy-2-methoxyphenyl)-5-[4-(2-sulfoethyl carbamoyl) phenyl]-2H-tetrazolium salt;

2,2'-dibenzothiazoyl-5,5'-bis [4-di(2-sulfoethyl)carbamoylphenyl]-3,3'-(3,3'-dimethoxy-4,4'-biphenylene)ditetrazolium salt; and 3-(4,5-dimethyl-2-thiazoyl)-2,5-diphenyl-2H-tetrazolium salt.

Further, a tetrazolium compound containing ring substituents having a benzene ring structure at two positions and a substituent not having a ring structure at one position on its tetrazole ring also can be used. Examples of such a tetrazolium compound include:

2,3-diphenyl-5-cyano tetrazolium salt;

2,3-diphenyl-5-carboxy tetrazolium salt;

2,3-diphenyl-5-methyltetrazolium salt; and 2,3-diphenyl-5-ethyl tetrazolium salt.

Among the above-described tetrazolium compounds, the tetrazolium compounds containing three ring substituents are preferable as described above. Among these, the tetrazolium compounds containing three ring substituents having a benzene ring structure and a large number of electron-withdrawing functional groups is more preferable, and 2-(4-iodophenyl)-3-(2,4-dinitrophenyl)-5-(2,4-disulfophenyl)-2H-tetrazolium salt is most preferable. It is to be noted here that the above-described tetrazolium compounds may be a salt or may have been ionized, for example.

As the FAOD, FAOD catalyzing a reaction represented by Formula (1) below preferably is used.

$$R^1\text{—CO—}CH_2\text{—NH—}R^2 + H_2O + O_2 \rightarrow R^1\text{—CO—CHO} + NH_2\text{—}R^2 + H_2O_2 \qquad (1)$$

In Formula (1), $R^1$ denotes a hydroxyl group or a residue derived from the sugar before glycation (i.e., sugar residue). The sugar residue ($R^1$) is an aldose residue when the sugar before glycation is aldose, and is a ketose residue when the sugar before glycation is ketose. For example, when the sugar before glycation is glucose, it takes a fructose structure after glycation by an Amadori rearrangement. In this case, the sugar residue ($R^1$) becomes a glucose residue (an aldose residue). This sugar residue ($R^1$) can be represented, for example, by —[CH(OH)]$_n$—CH$_2$OH where n is an integer of 0 to 6.

In Formula (1), $R^2$ is not particularly limited. However, when the substrate is a glycated amino acid, a glycated peptide, or a glycated protein, for example, there is a difference between the case where an α-amino group is glycated and the case where an amino group other than the α-amino group is glycated.

In Formula (1), when an α-amino group is glycated, $R^2$ is an amino acid residue or a peptide residue represented by Formula (2) below.

—CHR$^3$—CO—R$^4$ (2)

In Formula (2), $R^3$ denotes an amino-acid side chain group. $R^4$ denotes a hydroxyl group, an amino acid residue, or a peptide residue, and can be represented, for example, by Formula (3) below. In Formula (3), n is an integer of 0 or more, and $R^3$ denotes an amino-acid side chain group as in the above.

—(NH—CHR$^3$—CO)$_n$—OH (3)

In Formula (1), when an amino group other than the α-amino group is glycated (i.e., an amino-acid side chain group is glycated), $R^2$ can be represented by Formula (4) below.

—R$^5$—CH(NH—R$^6$)—CO—R$^7$ (4)

In Formula (4), $R^5$ denotes a portion other than the glycated amino group in the amino-acid side chain group. For example, when the glycated amino acid is lysine, $R^5$ is as follows.

—CH$_2$—CH$_2$—CH$_2$—CH$_2$—

For another example, when the glycated amino acid is arginine, $R^5$ is as follows.

—CH$_2$—CH$_2$—CH$_2$—NH—CH(NH$_2$)—

In Formula (4), $R^6$ denotes hydrogen, an amino acid residue, or a peptide residue, and can be represented, for example, by Formula (5) below. In Formula (5), n denotes an integer of 0 or more, and $R^3$ denotes an amino-acid side chain group as in the above.

—(CO—CHR$^3$—NH)$_n$—H (5)

In Formula (4), $R^7$ denotes a hydroxyl group, an amino acid residue, or a peptide residue, and can be represented, for example, by Formula (6) below. In Formula (6), n is an integer of 0 or more, and $R^3$ denotes an amino-acid side chain group as in the above.

—(NH—CHR$^3$—CO)$_n$—OH (6)

Examples of the FAOD include those produced by the following genera, for example: the genus *fusarium*, the genus *Gibberella*, the genus *Penicillium*, the genus *Armillaria*, the genus *Caldariomyces*, the genus *Ganoderma*, and the genus *Aspergillus*. Specific examples include *Fusarium oxysporum* S-1F4 (FERM BP-5010), *Fusarium oxysporum* f. sp. *lini* (IFO NO. 5880), *Fusarium oxysporum* f. sp. *batatas* (IFO NO. 4468), *Fusarium oxysporum* f. sp. *niveum* (IFO NO. 4471), *Fusarium oxysporum* f. sp. *cucumerium* (IFO NO. 6384), *Fusarium oxysporum* f. sp. *melongenae* (IFO NO. 7706), *Fusarium oxysporum* f. sp. *apii* (IFO NO. 9964), *Fusarium oxysporum* f. sp. *pini* (IFO NO. 9971), *Fusarium oxysporum* f. sp. *fragariae* (IFO NO. 31180), *Gibberella fujikuroi* (IFO NO. 6356, 6605), *Penicillium janthinellum* S-3413 (FERM BP-5475), *Penicillium janthinellum* (IFO NO. 4651, 6581, 7905), *Penicillium oxalicum* (IFO NO. 5748), *Penicillium javanicum* (IFO NO. 4639), *Penicillium chrysogenum* (IFO NO. 4897), *Penicillum cyaneum* (IFO NO. 5337), *Aspergillus terreus* (IFO NO. 6365), *Aspergillus terreus* GP-1 (FERM BP-5684), *Aspergillus oryzae* (IFO NO. 4242), and *Aspergillus oryzae* (IFO NO. 5710).

Furthermore, examples of commercially available FAOD include a product named Fructosyl-Amino Acid Oxidase (FAOX-E) (Kikkoman Corporation) and a product named Fructosyl Amine Oxidase (Asahi Chemical Industry Co., Ltd.), which specifically act on a glycated amino acid having a glycated α-amino group.

Hereinafter, the method of the present invention will be described in detail with reference to the following examples, in which a glycated protein in blood cells is measured.

First, whole blood itself is hemolyzed, or a blood cell fraction is separated from whole blood in the usual way such as centrifugation and then hemolyzed, so as to prepare a hemolyzed sample. The method of causing the hemolysis is not particularly limited, and can be, for example, a method using a surfactant, a method using ultrasonic waves, a method utilizing a difference in osmotic pressure, and a method using a freeze-thawing technique. Among these, the method using a surfactant is preferable because of its simplicity in operation, etc.

As the surfactant, for example, non-ionic surfactants such as polyoxyethylene-p-t-octylphenyl ether (e.g. Triton series surfactants), polyoxyethylene sorbitan alkyl ester (e.g. Tween series surfactants), polyoxyethylene alkyl ether (e.g. Brij series surfactants), and the like can be used. Specific examples are Triton X-100, Tween-20, Brij 35, and the like. The conditions of the treatment with the surfactant usually are as follows: when the concentration of blood cells in the solution to be treated is in the range from 1 to 10 vol %, the surfactant is added so that its concentration in the solution falls in the range from 0.01 to 5 wt %, and stirred at room temperature for about several seconds (about 5 seconds) to 10 minutes.

Next, a tetrazolium compound and sodium azide are added to the hemolyzed sample.

By adding the tetrazolium compound and sodium azide, the sensitivity becomes about 1.2 to 3 times greater than in the case where they are not added.

When the concentration of blood cells in the solution to be treated is in the range from 0.2 to 2 vol %, the tetrazolium compound preferably is added so that its concentration in the solution falls in the range from 0.005 to 400 mmol/l, more preferably from 0.02 to 100 mmol/l, and particularly preferably from 0.1 to 50 mmol/l. Specifically, when the tetrazolium compound is 2-(4-iodophenyl)-3-(2,4-dinitrophenyl)-5-(2,4-disulfophenyl)-2H-tetrazolium salt, it preferably is added so that its concentration falls in the range from 0.004 to 16 mmol/l, more preferably from 0.02 to 10 mmol/l, and particularly preferably from 0.1 to 5 mmol/l. Moreover, the tetrazolium compound may be used either alone or in combinations of two or more types.

Furthermore, the tetrazolium compound (A) and the sodium azide (B) are added so that they are present at a ratio (molar ratio A: B), for example, in the range from 20:3 to 20:12, preferably 20:5 to 20:11, and more preferably 20:6 to 20:10.

The tetrazolium compound and sodium azide may be added to the hemolyzed sample simply as they are. However, in terms of simplicity in operation etc., it is preferable to use a tetrazolium compound solution obtained by dissolving the tetrazolium compound in a solvent and a sodium azide solution obtained by dissolving the sodium azide in a solvent, or a liquid mixture containing both the tetrazolium compound and sodium azide (i.e., a tetrazolium compound-sodium azide liquid mixture).

The concentration of the tetrazolium compound (C) or the sodium azide (D) in the above-described respective solutions can be determined as appropriate depending on the diluting factor of the solutions when they are added to the hemolyzed sample, etc., but the concentration of the tetrazolium compound (C) is, for example, in the range from 0.6 to 10 mmol/l, preferably from 0.75 to 3 mmol/l, and more preferably from 1 to 2.4 mmol/l. When the liquid mixture is to be used, the liquid mixture contains the tetrazolium compound (C) and the sodium azide (D), for example, at a ratio (molar ratio C:D) in a range from 20:5 to 20:11, preferably 20:6 to 20:8.

As the solvent of the above-described solutions, Good's buffers such as MOPS, MES, MOPSO, DIPSO, TES, POPSO, and HEPES, a phosphate buffer, and the like can be used, for example. Among these, MES and MOPS are preferable. The pH of the solvent is, for example, in the range from 5.0 to 7.0, preferably 5.5 to 6.5, and more preferably 5.5. The concentration of the buffer is, for example, in the range from 1 to 100 mmol/l, preferably 1 to 10 mmol/l. The final concentration of the buffer after being added to the hemolyzed sample is, for example, in the range from 0.7 to 9 mmol/l, preferably from 0.8 to 4.5 mmol/l.

Moreover, the tetrazolium compound-sodium azide liquid mixture prepared preferably is left for a certain period before being added to the hemolyzed sample so as to be aged because this allows still further improvement in sensitivity. According to this aging treatment, the sensitivity becomes, for example, about 1.2 to 3 times greater than in the case where the aging treatment is not performed.

In the aging treatment, the treatment temperature preferably is in the range from 40° C. to 60° C., more preferably 50° C. to 60°, and the treatment period is, for example, at least 6 hours, preferably 6 to 120 hours, and more preferably 6 to 72 hours.

After the tetrazolium compound and sodium azide are added to the hemolyzed sample simply as they are or as the above-described solution, the pretreatment of the hemolyzed sample is carried out, usually by incubating the sample at 40° C. to 60° C. for 6 to 72 hours. By pretreating the sample with the tetrazolium compound, the influence of reducing substances and the like contained in the sample on a redox reaction can be eliminated, whereby the accuracy of measurement is improved. Although the tetrazolium compound contributes to the improvement in the accuracy of measurement as described above, it is necessary that sodium azide coexists with the tetrazolium compound in order to achieve the improvement in measurement sensitivity as an object of the present invention. By using the tetrazolium compound and sodium azide in combination, an effect peculiar to the present invention can be obtained.

Next, the pretreated hemolyzed sample containing the tetrazolium compound and sodium azide is treated with a protease. This protease treatment is carried out so that FAOD to be used later can act on the analyte more easily.

The type of the protease is not particularly limited, and for example, serine proteases, thiol proteases, metalloproteinases, and the like can be used. Specifically, trypsin, proteinase K, chymotrypsin, papain, bromelain, subtilisin, elastase, aminopeptidase, and the like are preferable. In the case where the glycated protein to be degraded is a glycated hemoglobin, the protease is the one that degrades the glycated hemoglobin selectively, and bromelain, papain, trypsin derived from porcine pancreas, metalloproteinases, and protease derived from *Bacillus subtilis*, and the like are preferable. Examples of the protease derived from *Bacillus subtilis* include a product named Protease N (e.g., Fluka Chemie AG), a product named Protease N "AMANO" (Amano Enzyme Inc.), and the like. Examples of the metalloproteinases include metalloproteinase (EC 3. 4. 24. 4) derived from the genus *Bacillus* (e.g., a product named Toyoteam manufactured by Toyobo Co., Ltd.) and the like. Among these, metalloproteinases, bromelain, and papain are more preferable, and metalloproteinases are particularly preferable. Thus, a degradation product of a specific protein can be prepared selectively by using a protease that degrades the protein selectively. The protease treatment usually is carried out in a buffer, and the conditions of the treatment are determined as appropriate depending on the type of the protease used, the type and the concentration of the glycated protein as an analyte, etc.

As the buffer, CHES, CAPSO, CAPS, phosphate, Tris, EPPS, HEPES buffers, and the like can be used, for example. The pH of the buffer is, for example, in the range from 6 to 13, preferably from 7 to 11. Moreover, the final concentration of the buffer in the solution subjected to the protease treatment is, for example, in the range from 1.0 to 10 mmol/l.

Specifically, when the pretreated hemolyzed sample is treated using a metalloproteinase as the protease, the protease treatment usually is carried out under the conditions as follows: the concentration of the metalloproteinase in the reaction solution in the range from 0.1 to 40 MU/l; the concentration of blood cells in the reaction solution in the range from 0.05 to 15 vol %; the reaction temperature in the range from 15° C. to 37° C.; the reaction period in the range from 1 minute to 24 hours; and the pH in the range from 6 to 12.

Furthermore, when the pretreated hemolyzed sample is treated using protease K as the protease, the protease treatment usually is carried out under the conditions as follows: the concentration of the protease in the reaction solution in the range from 10 to 300 KU/l; the concentration of blood cells in the reaction solution in the range from 0.05 to 15 vol %; the reaction temperature in the range from 15° C. to 37° C.; the reaction period in the range from 1 minute to 24 hours; and the pH in the range from 6 to 12. Moreover, the type of the buffer is not particularly limited, and for example, Tris-HCl buffer, EPPS buffer, PIPES buffer, and the like can be used.

Next, the degradation product obtained by the protease treatment is treated with the FAOD. The reaction shown by Formula (1) above is catalyzed by this FAOD treatment.

Similarly to the above-described protease treatment, this FAOD treatment preferably is carried out in a buffer. The conditions of the FAOD treatment are determined as appropriate depending on the type of the FAOD used, the type and the concentration of the glycated protein as an analyte, and the like.

Specifically, the FAOD treatment is carried out, for example, under the following conditions: the concentration of the FAOD in the reaction solution in the range from 50 to 50,000 U/l, the concentration of the blood cells in the reaction solution in the range from 0.01 to 1 vol %, the reaction temperature in the range from 15° C. to 37° C., the reaction period in the range from 1 to 60 minutes, and the pH in the range from 6 to 9. Moreover, the type of the buffer is not particularly limited, and the same buffers as in the protease treatment also can be used in the FAOD treatment.

Next, the hydrogen peroxide formed by the FAOD treatment is measured by a redox reaction using POD and the color-developing substrate.

As the color-developing substrate, N-(carboxymethylaminocarbonyl)-4,4'-bis(dimethylamino)diphenylamine sodium salt, orthophenylenediamine (OPD), a substrate in which a Trinder's reagent and 4-aminoantipyrine are combined, and the like can be used, for example. Examples of the Trinder's reagent include phenols, phenol derivatives, aniline derivatives, naphthols, naphthol derivatives, naphthylamine, and naphthylamine derivatives. Furthermore, in place of the aminoantipyrine, it is possible to use aminoantipyrine derivatives, vanillin diamine sulfonic acid, methylbenzothiazolinone hydrazone (MBTH), sulfonated methylbenzothiazolinone hydrazone (SMBTH), and the like. Among these color-developing substrates, N-(carboxymethylaminocarbonyl)-4,4'-bis (dimethylamino)diphenylamine sodium salt is particularly preferable.

The redox reaction usually is carried out in a buffer. The conditions of the reaction are determined as appropriated depending on the concentration of the hydrogen peroxide formed, etc. The conditions are usually as follows: the concentration of the POD in the reaction solution in the range from 10 to 100,000 IU/l; the concentration of the color-developing substrate in the range from 0.005 to 30 mmol/l; the reaction temperature in the range from 15° C. to 37° C.; the reaction period in the range from 0.1 to 30 minutes; and the pH in the range from 5 to 9. Moreover, the type of the buffer is not particularly limited, and for example, the same buffers as in the protease treatment and the FAOD treatment can be used.

In the redox reaction, for example, when the color-developing substrate is used, the amount of the hydrogen peroxide can be determined by measuring the degree of the color developed (i.e. absorbance) in the reaction solution with a spectrophotometer. Then, for example, the amount of the glycated protein in the sample can be determined using the concentration of the hydrogen peroxide and a calibration curve or the like.

The degree of the color developed can be determined not only by measuring the absorbance but also by optical measurement such as measurement of reflectance or the like. Moreover, the amount of the hydrogen peroxide can be determined not only by the above-described enzymatic method using the POD etc. but also by an electrical method, for example.

Thus, by adding a tetrazolium compound and sodium azide, the measurement of a glycated protein using a redox reaction can be carried out with high sensitivity.

The order of adding a tetrazolium compound and sodium azide is not particularly limited. However, since aging them enhances the effect of the present invention, they preferably are mixed with each other in advance.

Furthermore, as described above, the analyte is not particularly limited as long as a redox reaction is utilized. Examples of the analyte other than the above-described glycated proteins include glycated peptides, glycated amino acids, glucose, cholesterol, uric acid, creatinine, sarcosine, and glycerol. When the amount of each of the above-described examples of the analyte is measured, measurement can be carried out, for example, by adding a tetrazolium compound and sodium azide to a measurement sample in the same manner as described above, then forming a reducing substance or an oxidizing substance derived from the analyte in the following manner, and measuring the amount of the reducing substance or oxidizing substance using a redox reaction.

When the measurement is carried out by forming hydrogen peroxide, the hydrogen peroxide may be formed, for example, by action of: a glucose oxidase on the glucose; a cholesterol oxidase on the cholesterol; a uricase on the uric acid; a sarcosine oxidase on the creatinine; a sarcosine oxidase on the sarcosine; or a glycerol oxidase on the glycerol; respectively. The amount of the hydrogen peroxide can be measured in the same manner as above. Moreover, glycated peptides and glycated amino acids can be measured, for example, in the same manner as in the measurement of the glycated proteins.

Furthermore, when the amount of the analyte is determined by forming a reducing substance derived from the analyte, measuring the amount of the reducing substance by a redox reaction, and then determining the amount of the analyte from the amount of the reducing substance, the measurement can be carried out, for example, in the following manner.

When the analyte is glucose, for example, a reducing substance such as NADH or NADPH is formed using glucose dehydrogenase in the presence of NAD, NADP, or the like. Then, the NADH or NADPH as a reducing substance derived from the analyte is measured by a redox reaction, using, for example, diaphorase and a substrate that develops color by reduction. Then, as described above, the amount of the analyte in the sample can be determined, for example, using the concentration of the reducing substance derived from the analyte and a calibration curve or the like. Furthermore, for example, cholesterol dehydrogenase can be used when the analyte is cholesterol, and sarcosine dehydrogenase can be used when the analyte is sarcosine.

As the substrate that develops color by reduction, although not particularly limited, for example, 2,6-dichlorophenolindophenol and the like can be used. Moreover, in order to obtain measured values with more excellent reliability, it is preferable to measure an absorbance before measuring the reducing substance derived from the analyte, for example.

EXAMPLES

Example 1 and Comparative Example 1

First, blood having a Hb concentration of 150 g/l (HbA1c 5.8%) was hemolyzed by adding 0.3 ml of the following hemolysis reagent to prepare a hemolyzed sample. Then, 65 μl of the following first reagents containing 3g/l sodium azide aqueous solution at predetermined concentrations (0 mmol/l, 0.30 mmol/l, 0.616 mmol/l, 0.924 mmol/l, 1.232 mmol/l, and 1.54 mmol/l) were added to mixtures of 25 μl of the hemolyzed sample and 20 μl of purified water, respectively. The resultant mixtures were incubated at 37° C. for 5 minutes. The first reagents were aged at 50° C. for 20 hours before being added to the hemolyzed sample. Subsequently, 45 μl of the following color-developing reagent A further was added, and the resultant mixtures were incubated at 37° C. for 3 minutes. Thereafter, with regard to the thus-obtained reaction solutions, the absorption was measured at the main wavelength of 751 nm and the sub-wavelength of 805 nm using a biochemical automatic analysis apparatus (product name Bio Majesty, manufactured by Japan Electron Optics Laboratory Co. Ltd.). The results are shown in Table 1. The mixture containing no sodium azide (0 g/l) was regarded as Comparative Example 1.

| (Hemolysis Reagent: pH 9.0) | |
|---|---|
| CHES buffer | 380 mmol/l |
| Polyoxyethylene lauryl ether | 24 g/l |

| (First Reagent) | | |
|---|---|---|
| 100 mmol/l | MOPS (pH 6.0) | 0.15 ml |
| 13 MU/l | metalloproteinase | 0.60 ml |
| 10 mmol/l | tetrazolium compound | 0.60 ml |
| 20 mmol/l | $CaCl_2$ | 0.045 ml |
| 3 g/l | $NaN_3$ | predetermined amount |
|  | distlled water | remaining portion |
|  | total amount | 3.0 ml |

As the metalloproteinase, metalloproteinase derived from the genus *Bacillus* was used. As the tetrazolium compound, 2-(4-iodophenyl)-3-(2,4-dinitrophenyl)-5-(2,4-disulfophenyl)-2H-tetrazolium salt (product name WST-3, manufactured by Dojindo Laboratories, hereinafter referred to as "WST-3") was used.

| (Color-Developing Reagent A) | |
|---|---|
| FAOD (product name Fructosyl Amino Acid Oxidase, ARKRAY, INC., hereinafter the same) | 26.0 KU/l |
| POD (Toyobo Co., Ltd., hereinafter the same) | 77.6 KU/l |
| Color-developing substrate (product name DA-64, Wako Pure Chemical Industries, Ltd., hereinafter the same) | 0.052 mmol/l |
| Tris-HCl buffer (pH 6.9) | 200 mmol/l |

TABLE 1

| | Final concentration of sodium azide in first reagent (mmol/l) | Concentration of tetrazolium compound in first reagent (mmol/l) | Absorbance |
|---|---|---|---|
| Com. Ex. 1 | 0 | 2 | 0.0124 |
| Ex. 1 | 0.300 | 2 | 0.0476 |
|  | 0.616 | 2 | 0.0518 |
|  | 0.924 | 2 | 0.0475 |
|  | 1.232 | 2 | 0.0418 |
|  | 1.540 | 2 | 0.0275 |

As can be seen from Table 1, in Example 1, by conducting the measurement in the presence of the tetrazolium compound and sodium azide, the absorbance higher than that in Comparative Example 1 was obtained because the amount of the color developed by the color-developing substrate DA-64 increased. Thus, it can be said that the method according to the present invention can improve the measurement sensitivity.

Example 2 and Comparative Example 2

In Example 2, WST-3 and sodium azide were added so that they were present at various ratios, and further improvement in measurement sensitivity by aging them was confirmed.

(Reagent Sample)

Reagent samples (A) to (E) were prepared by mixing WST-3 and sodium azide so that they were present at the following ratios. Then, the samples (B) to (E) were incubated at 40° C. for 20 hours. Subsequently, the samples (A) to (E) were maintained at the temperature not higher than 4° C. and metalloproteinase was added to the samples so that its concentration became 2.66 MU/l.

(Ratio Between WST-3 and Sodium Azide)

Example 2

| | (A) | (B) | (C) | (D) | (E) |
|---|---|---|---|---|---|
| WST-3 (mmol/l) | 2.0 | 2.0 | 2.0 | 2.7 | 1.3 |
| $NaN_3$ (mmol/l) | 0.7 | 0.7 | 1.4 | 1.4 | 0.7 |
| WST-3:$NaN_3$ (molar ratio) | 3:1 | 3:1 | 1.43:1 | 1.9:1 | 1.9:1 |
| MOPS pH 6.5 (mmol/l) | 5.5 | 5.5 | 5.5 | 5.5 | 5.5 |
| $CaCl_2$ (mmol/l) | 5.5 | 5.5 | 5.5 | 5.5 | 5.5 |
| NaCl (mmol/l) | 0.33 | 0.33 | 0.33 | 0.33 | 0.33 |
| Aging | — | ○ | ○ | ○ | ○ |

(Hemolyzed Solution)

Distilled water was added to blood cells. The mixture was frozen and then thawed to hemolyze the blood cells In the hemolyzed solution thus obtained, the Hb concentration was 100 g/l and HbA1c was 4.9%.

The hemolysed solution thus prepared was pretreated by adding the following pretreatment reagent so as to have the following compositions.

| | Hb concentration | | | |
|---|---|---|---|---|
| | 6.7 g/l | 13.4 g/l | 20.1 g/l | 33.5 g/l |
| Hemolyzed solution | 50 μl | 100 μl | 150 μl | 250 μl |
| Pretreatment reagent | 434 μl | 434 μl | 434 μl | 434 μl |
| Distilled water | 266 μl | 216 μl | 166 μl | 66 μl |
| | total amount 750 μl | | | |

The pretreatment reagent was prepared by adding a surfactant to a buffer so that its concentration became 20 wt %. As the surfactant, polyoxyethylene lauryl ether (product name Nikkol, manufactured by Nihon Surfactant Kogyo K.K.) was used. The buffer used was a mixed buffer (pH 9.5) obtained by mixing a glycinamide buffer and a glycine solution so that the final concentration of glycinamide became 200 mM and the final concentration of glycine became 40 mM.

| (Color-Developing Reagent B) | |
|---|---|
| FAOD | 25.9 KU/l |
| POD | 77.6 KU/l |

-continued

| (Color-Developing Reagent B) | |
|---|---|
| Color-developing substrate | 0.0518 mmol/l |
| Tris-HCl buffer (pH 6.9) | 200 mmol/l |

(Measuring Procedure)

First, the pretreated hemolyzed solutions were diluted 2.4-fold with distilled water, and 20 μL of these diluted solutions were mixed with 60 μl of each of the reagent samples and 50 μl of the color-developing reagent B. The resultant mixtures were allowed to react at 37° C. for 15 minutes. Thereafter, the absorption was measured at the main wavelength of 751 nm and the sub-wavelength of 805 nm using a biochemical automatic analysis apparatus (product name JCA-BM 8, manufactured by Japan Electron Optics Laboratory Co. Ltd.). The results are shown in Table 2 below and in the graph shown in FIG. 1. The graph of FIG. 1 shows the relationship between a molar ratio between the tetrazolium compound and sodium azide, a Hb concentration, and an absorbance.

TABLE 2

| | Example 2 | | | | |
|---|---|---|---|---|---|
| Hb concentration | (A) | (B) | (C) | (D) | (E) |
| 0 g/l | 0.1542 | 0.1628 | 0.1469 | 0.1403 | 0.1647 |
| 6.7 g/l | 0.0034 | 0.0101 | 0.0087 | 0.0099 | 0.0097 |
| 13.4 g/l | 0.0063 | 0.0180 | 0.0146 | 0.0173 | 0.0171 |
| 20.1 g/l | 0.0094 | 0.0259 | 0.0202 | 0.0249 | 0.0243 |
| 33.5 g/l | 0.0127 | 0.0384 | 0.0278 | 0.0374 | 0.0349 |

As shown in Table 2 and FIG. 1, high absorbance was exhibited by adding the tetrazolium compound and sodium azide. Moreover, further improvement in absorbance was achieved by conducting incubation (aging) ((B) to (E)). Moreover, since the absorbance increased in keeping with the Hb concentration, it can be said that the absorbance did not increase due to the absorption of the tetrazolium compound and sodium azide themselves but increased because the absorbance of the color-developing substrate DA-64 increased by adding the tetrazolium compound and sodium azide. Furthermore, the significant increase in absorbance was observed when the tetrazolium compound and sodium azide were added so that they were present at the molar ratio of 3:1 and they were aged as well. Thus, because the amount of color developed by the color-developing substrate increased by adding the tetrazolium compound and sodium azide and it increased still further by conducting aging, it can be said that the measurement sensitivity was improved.

Example 3

In Example 3, a tetrazolium compound and sodium azide were aged in a solution to examine how this affects the improvement in measurement sensitivity.

First, a liquid mixture containing 3.33 mmol/l of WST-3 and 0.0833 g/l of sodium azide was prepared and then aged by being incubated at 60° C. Then, samples were taken predetermined periods (0 hour, 1 hour, 6 hours, 14 hours, 16 hours, and 18 hours) after the start of the incubation. These samples were used as reagent samples.

On the other hand, a hemolyzed solution (Hb concentration: 100 g/l, HbA1c: 4.9%) was prepared in the same manner as in Example 2. Then, predetermined amounts (2 μl, 5 μl, 10 μl, 20 μl, and 30 μl) of hemolyzed solution were mixed with 300 μl of the following pretreatment reagent to prepare substrate Hb solutions (A to E).

(Pretreatment Reagent)

Figure 2:
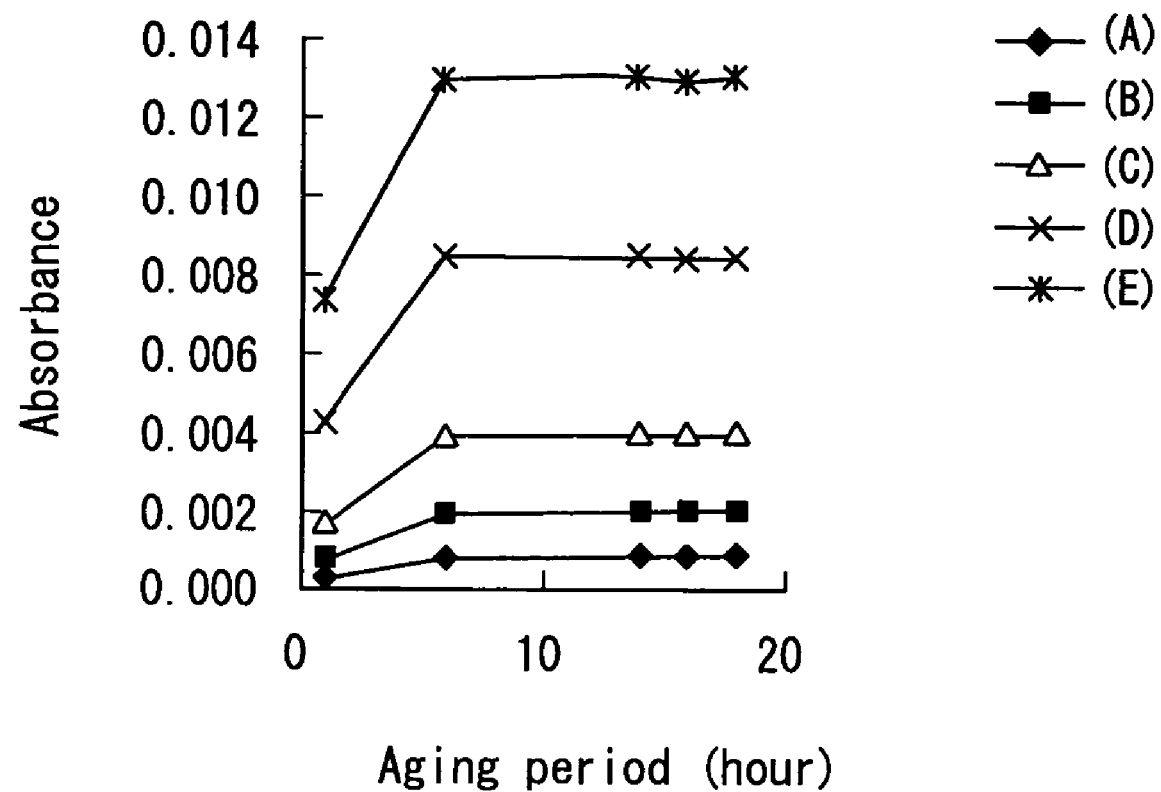
FIG. 2 is a graph showing the relationship between an aging period and an absorbance of a solution containing a tetrazolium compound and sodium azide in another example of a method for measurement according the present invention.

Liquid Mixture (pH 9.4) of 80 mmol/l CHES and 30 mmol/l MOPS 9 g/l of Polyoxyethylene Lauryl Ether First, the respective substrate Hb solutions were diluted 2-fold with distilled water, and 20 μL of these diluted solutions were mixed with 65 μl of each of the following second reagents respectively containing the above-described reagent samples and 45 μl of the color-developing reagent C. The resultant mixtures were allowed to react at 37° C. for 15 minutes. Thereafter, the absorption at the main wavelength of 751 nm and the sub-wavelength of 805 nm was measured using the above-described biochemical automatic analysis apparatus. The results are shown in Table 3 below and FIG. 2. FIG. 2 is a graph showing the relationship between an aging period and an absorbance.

| (Second Reagent) | | |
|---|---|---|
| 1 mol/l | $CaCl_2$ | 0.035 ml |
| 5 mol/l | NaCl | 0.280 ml |
| 30 mmol/l | MES (pH 5.5) | 1.40 ml |
| 100 MU/l | metalloproteinase | 0.7 ml |
| | distlled water | 0.385 ml |
| | total amount | 7.0 ml |

| (Color-Developing Reagent C) | |
|---|---|
| FAOD | 25.9 KU/l |
| POD | 77.6 KU/l |
| Color-developing substrate | 0.0518 mmol/l |
| Tris-HCl buffer (pH 7.0) | 300 mmol/l |

TABLE 3

| | Final concentration of Hb | | | | |
|---|---|---|---|---|---|
| Aging period (hour) | (A) 0.10 g/l | (B) 0.25 g/l | (C) 0.50 g/l | (D) 0.96 g/l | (E) 1.40 g/l |
| 0 | 0.0003 | 0.0007 | 0.0015 | 0.0037 | 0.0065 |
| 1 | 0.0003 | 0.0008 | 0.0017 | 0.0042 | 0.0073 |
| 6 | 0.0008 | 0.0020 | 0.0039 | 0.0084 | 0.0129 |
| 14 | 0.0009 | 0.0020 | 0.0039 | 0.0084 | 0.0130 |
| 16 | 0.0008 | 0.0020 | 0.0039 | 0.0083 | 0.0128 |
| 18 | 0.0008 | 0.0020 | 0.0039 | 0.0083 | 0.0129 |

As shown in Table 3 and FIG. 2, it was found that further improvement in measurement sensitivity can be achieved by using the solution containing the tetrazolium compound and sodium azide after aging it, regardless of the Hb concentration. Furthermore, the sensitivity reached its maximum when the aging period was 6 hours or longer.

Example 4

In Example 4, a tetrazolium compound and sodium azide were aged in a solution to examine how this affects the improvement in measurement sensitivity.

First, the following liquid mixture containing WST-3 and sodium azide was prepared and then aged by being incubated at predetermined temperatures (30° C., 40° C., 50° C., and 60° C.) for predetermined periods (0 hour, 6 hours, 15 hours, 24 hours, 48 hours, and 72 hours) to prepare reagent samples.

| (Composition of Liquid Mixture) | |
| --- | --- |
| WST-3 | 2.20 mmol/l |
| Sodium azide | 0.05 g/l |
| MOPS (pH 6.5) | 5.50 mmol/l |
| CaCl$_2$ | 5.50 mmol/l |
| NaCl | 330 mmol/l |

Figure 3:
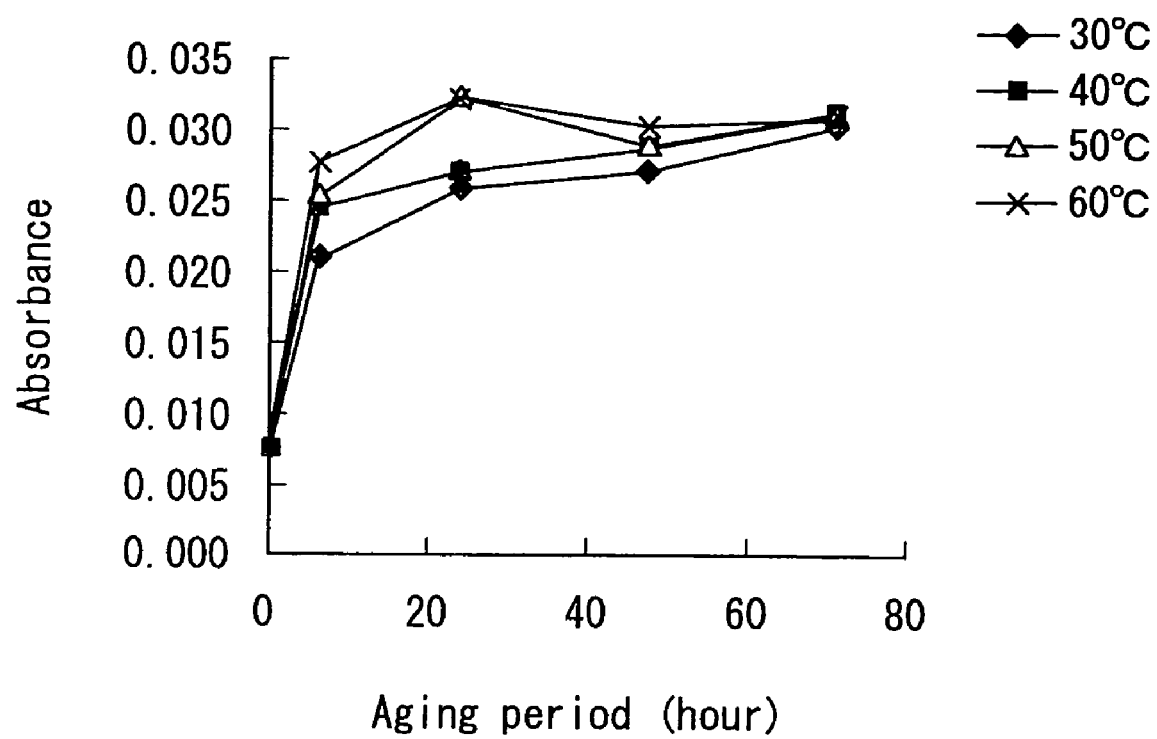
FIG. 3 is a graph showing the relationship between an aging period and an absorbance of a solution containing a tetrazolium compound and sodium azide in still another example of a method for measurement according the present invention.

On the other hand, substrate Hb solutions (Hb concentration: 100 g/l) were prepared in the same manner as in Example 2 and diluted 2-fold (by volume) with purified water to prepare diluted solutions. On the other hand, metalloproteinase solutions were prepared by mixing 9 ml of the above-described respective reagent samples with 1 ml of metalloproteinase (2.7 MU/l). Then, 20 μL of the diluted solutions were mixed with 65 μl of each of the metalloproteinase solutions and 45 μl of the color-developing reagent A. The resultant mixtures were allowed to react at 37° C. for 15 minutes. Thereafter, the absorption was measured at the main wavelength of 751 nm and the sub-wavelength of 805 nm using the above-described biochemical automatic analysis apparatus. The results are shown in Table 4 below and FIG. 3. FIG. 3 is a graph showing the relationship between an aging period and an absorbance.

TABLE 4

| Aging period | Aging temperature | | | |
| --- | --- | --- | --- | --- |
| (hour) | 30° C. | 40° C. | 50° C. | 60° C. |
| 0 | 0.0078 | 0.0078 | 0.0078 | 0.0078 |
| 6 | 0.0211 | 0.0244 | 0.0253 | 0.0277 |
| 24 | 0.0259 | 0.0270 | 0.0323 | 0.0320 |
| 48 | 0.0271 | 0.0286 | 0.0288 | 0.0301 |
| 72 | 0.0302 | 0.0311 | 0.0311 | 0.0308 |

As shown in Table 4 and FIG. 3, the absorbance increased rapidly when the aging was conducted at 60° C. Therefore, it can be said that the measurement sensitivity can be improved with shorter period of aging as the aging temperature becomes higher.

INDUSTRIAL APPLICABILITY

As specifically described above, the method for measurement using a redox reaction according to the present invention is excellent in measurement sensitivity because it uses a tetrazolium compound and sodium azide. Therefore, by applying the method of the present invention to, for example, the measurement of HbA1c contained in erythrocytes, it becomes possible to realize the measurement with higher accuracy than in conventional methods, which further increases the importance of HbA1c as an index in the diagnosis and the like of diabetes.

The invention claimed is:

1. A method of measuring an analyte in a sample using a redox reaction, comprising:
   aging a solution containing a tetrazolium compound and sodium azide at a temperature of at least 20° C. and not higher than 60° C. for 6 to 120 hours;
   then adding the aged solution to the sample;
   measuring an amount of a reducing substance or an oxidizing substance derived from the analyte in the presence of the tetrazolium compound and the sodium azide using the redox reaction; and
   determining an amount of the analyte from the amount of the reducing substance or oxidizing substance thus measured,
   wherein the tetrazolium compound (A) and the sodium azide (B) are present at a ratio (molar ratio A:B) in a range from 20:3 to 20:12, and
   the analyte is at least one selected from the group consisting of glycated proteins, alycated peptides, and glycated amino acids.

2. The method according to claim 1, wherein a final concentration of the tetrazolium compound in a reaction solution of the redox reaction is in a range from 0.5 to 2.5 mmol/l, and a final concentration of the sodium azide in the reaction solution is in a range from 0.13 to 1.3 mmol/l.

3. The method according to claim 1, wherein the tetrazolium compound is 2-(4-iodophenyl)-3-(2,4-dinitrophenyl)-5-(2,4-disulfophenyl)-2H-tetrazolium salt.

4. The method according to claim 1, wherein the glycated proteins are glycated hemoglobins.

5. The method according to claim 1, wherein the oxidizing substance derived from the analyte is hydrogen peroxide.

6. The method according to claim 5, wherein the hydrogen peroxide is formed by a reaction between a glycation site of a glycated protein and a fructosyl amino acid oxidase.

7. The method according to claim 5, wherein the amount of the hydrogen peroxide as the oxidizing substance is measured using an oxidase and a substrate that develops color by oxidation.

8. The method according to claim 7, wherein the amount of the hydrogen peroxide is measured by optical measurement of a degree of color developed by the substrate that develops color by oxidation.

9. The method according to claim 8, wherein the optical measurement is measurement of an absorbance or a reflectance.

10. The method according to claim 1, wherein the solution containing the tetrazolium compound and the sodium azide is aged at a temperature of at least 40° C.

11. The method according to claim 1, wherein the solution containing the tetrazolium compound and the sodium azide is aged at a temperature in a range from 40° C. to 60° C.

* * * * *